(12) United States Patent
Bayer

(10) Patent No.: US 11,931,246 B2
(45) Date of Patent: *Mar. 19, 2024

(54) INJECTOR FOR INTRAOCULAR LENSES

(71) Applicant: OPHTHALMO PRO GMBH, St. Ingbert (DE)

(72) Inventor: Alexander Bayer, Düsseldorf (DE)

(73) Assignee: OPHTHALMO PRO GMBH, St. Ingbert (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/248,639

(22) PCT Filed: Nov. 23, 2020

(86) PCT No.: PCT/EP2020/083025
§ 371 (c)(1),
(2) Date: Apr. 11, 2023

(87) PCT Pub. No.: WO2022/078617
PCT Pub. Date: Apr. 21, 2022

(65) Prior Publication Data
US 2023/0310146 A1 Oct. 5, 2023

(30) Foreign Application Priority Data
Oct. 13, 2020 (DE) .......................... 102020126789.4

(51) Int. Cl.
*A61F 2/16* (2006.01)
(52) U.S. Cl.
CPC .................................. *A61F 2/1672* (2013.01)

(58) Field of Classification Search
CPC ........ A61F 2/16; A61F 2/1672; A61F 2/1664; A61F 2/1662; A61F 2/1691; A61F 2/1678
See application file for complete search history.

(56) References Cited

U.S. PATENT DOCUMENTS

| 6,106,496 A * | 8/2000 | Arnissolle | A61M 25/10182 604/207 |
| 2009/0112223 A1* | 4/2009 | Downer | A61F 2/1667 606/107 |

FOREIGN PATENT DOCUMENTS

| CN | 202021009293 U | 6/2020 |
| CN | 202010500344 A | 12/2021 |

(Continued)

*Primary Examiner* — Vi X Nguyen
(74) *Attorney, Agent, or Firm* — DINSMORE & SHOHL LLP

(57) ABSTRACT

An intraocular lens implantation injector has a base body and elongated actuation element projecting into a base body rear section, movably guided along an actuation axis. Actuation element movement is generated selectively by axial push actuation or screw actuation about the axis. The actuation element features an external thread at least on one section. A switch element arranged to the base body is rotatable about or displaceable along the axis. The switch element features a spring arm, having an inner surface thread engagement structure facing the external thread. The base body inner surface forms an operative contact with a spring arm outer surface. The inner and/or outer surface is angularly inclined to the axis, or the inner surface features an inner radius varying circumferentially at least in sections about the axis. Switch element rotation/displacement generates spring arm elastic deformation towards/away from the axis, for selective thread engagement structure engagement.

14 Claims, 5 Drawing Sheets

(56) References Cited

FOREIGN PATENT DOCUMENTS

| EP | 2649962 A1 | 10/2013 |
| EP | 3476375 A1 | 5/2019 |
| WO | 2019195951 A1 | 10/2019 |

* cited by examiner

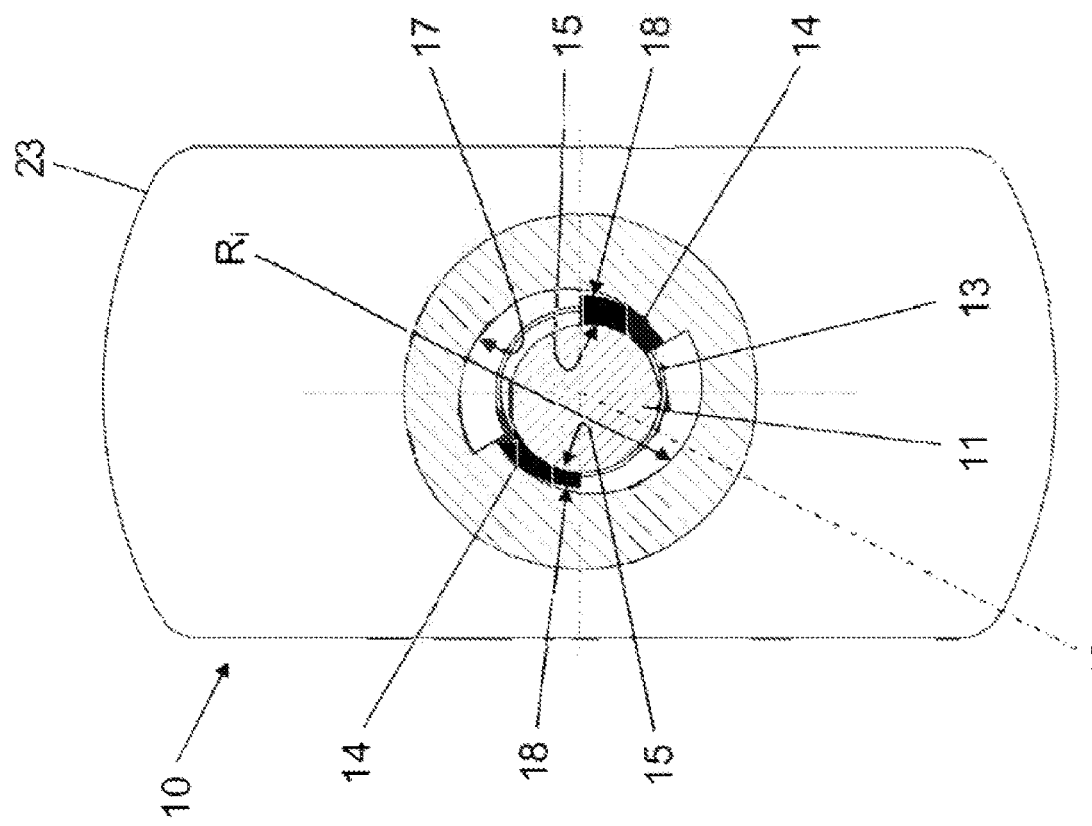
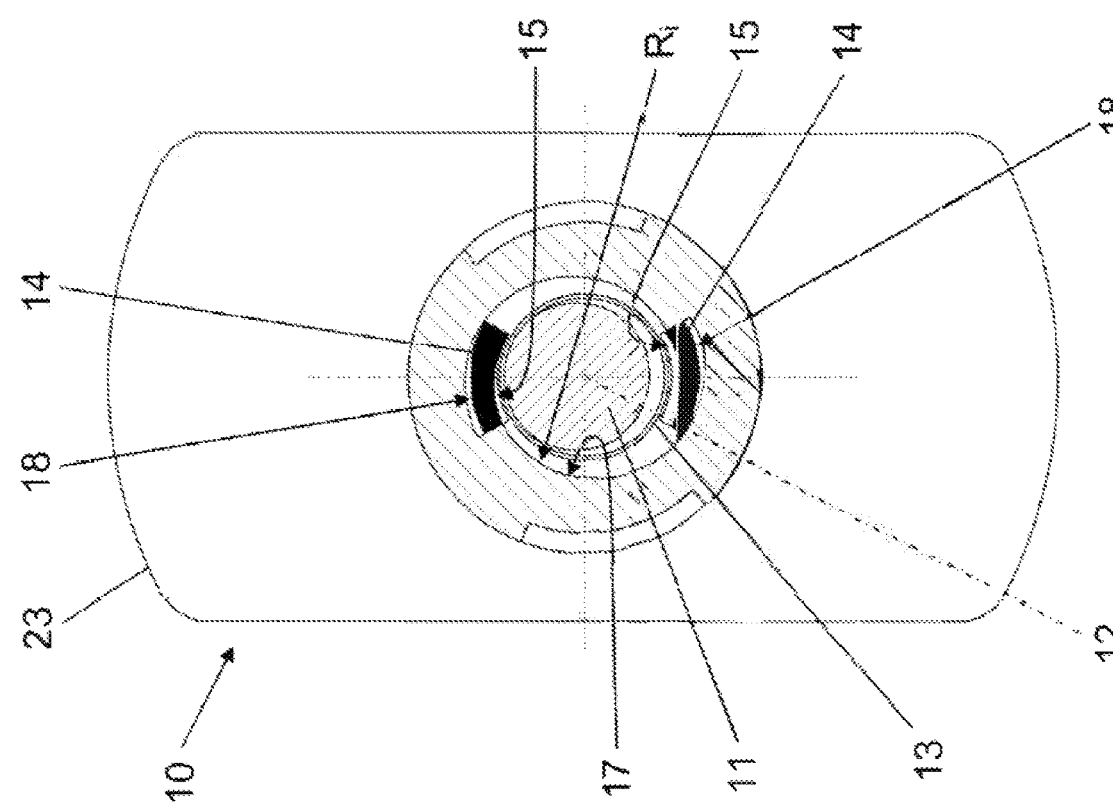

INJECTOR FOR INTRAOCULAR LENSES

CROSS-REFERENCE TO RELATED APPLICATIONS

This application is the U.S. National Stage of PCT/EP2020/083025 filed on Nov. 23, 2020, which claims priority to German Patent Application 102020126789.4 filed on Sep. 17, 2019, the entire content of both are incorporated herein by reference in their entirety.

FIELD OF THE INVENTION

The invention relates to an injector for implantation of an intraocular lens in a human or animal eye, having a base body and an elongated actuation element, which projects at least in sections into a rear section of the base body and which is movably guided in an actuation axis, and wherein a movement of the actuation element into the base body can be generated selectively by means of a push actuation along the actuation axis or by means of a screw actuation about the actuation axis, and wherein the actuation element features an external thread at least on one section, whereas a switch element is attached to the base body.

BACKGROUND OF THE INVENTION

Injectors for the implantation of intraocular lenses into a human eye are well known. For this purpose, an intraocular lens can either be inserted into the injector via a lens cartridge with an intraocular lens inserted into it shortly before the lens is inserted into the eye, in order to expel the intraocular lens from an anterior ejection nozzle into the posterior chamber of the eye after subsequent addition of a viscoelastic. The ejection nozzle forms the open end of a lens guide of the injector, which is located at the front of the base body.

In the base body, a piston is movably guided along the actuation axis, and the piston, which is connected to the actuation element in front of each other along the actuation axis, can come into contact with the intraocular lens and expel it through the ejection nozzle when the actuation element is advanced and thus transferred to the piston in the direction of the ejection nozzle.

In order to move the piston in a controlled manner within the base body of the injector and, advancing further in the direction of the ejection nozzle, also through the lens guide, the actuation element is provided, which projects into the base body in such a way that, when the actuation element is advanced in the actuation axis, the piston first contacts the intraocular lens and can then be moved together with the intraocular lens in the direction of the ejection nozzle until the intraocular lens is ejected into the posterior eye chamber.

Injectors of the newer type are used as disposable injectors and are disposed of after single use and ejection of the pre-loaded intraocular lens. This type of injector is generally referred to as pre-load system.

Sliding the actuation element into a rear opening in the base body is usually done manually by the operator, i.e. the ophthalmologist. Injectors are known, which, in a first operating mode, enable a pure pushing movement, which is manually introduced into the actuation element, and, in a second operating mode, enable a rotary movement, which is introduced into the same actuation element in order to move the actuation element along the actuation axis. In this respect, injectors of newer design are capable of both push and screw actuation, for which purpose a corresponding device for switching the operating mode is provided on the injector.

For example, EP 3 476 375 A1 reveals a design of an injector for the implantation of an intraocular lens, and the actuation element can either be retracted into the base body by direct rear insertion, or a positioning element is actuated by a screw movement, the positioning element having a direct threaded connection with an external thread of the actuation element. This means that when the actuation element is manually pushed into the base body, the positioning element rotates freely. Thus, if the actuation element is driven into the base body either by pushing on the back of the actuation element or by rotating the positioning element, the actuation element can, in contact with the piston, expel the intraocular lens from the ejection nozzle at the front. The positioning element must have a direct threaded connection with the actuation element to implement this principle of operation.

The WO 2019/195951 A1 reveals a further design of an injector for the implantation of an intraocular lens into a human or animal eye, having a base body into which an elongated actuation element projects in sections at the rear and is movably guided in an actuation axis, and wherein a movement of the actuation element into the base body can be generated optionally by means of a push actuation of the actuation element along the actuation axis or by means of a screw actuation of the actuation element about the actuation axis, for which purpose the actuation element features an external thread at least on one section. In order to switch over between the push actuation and the screw actuation of the actuation element, two opposite folding and unfolding wing handles are provided, wherein the unfolded position allows the operating mode to be switched to push actuation and in a folded position to screw actuation. In the operating mode of the push actuation the foldable wing handles can be used as finger grips, so that an ophthalmologist can grip the injector at the wing handles between the index finger and the middle finger, in order to finally push the actuation element into the base body with the thumb at the back. Once the wing handles are folded, the actuation element can be screwed into the base body by holding the base body in a first hand of the ophthalmologist and screwing the actuation element with the second hand of the ophthalmologist.

Adjustment of the injector for either push or screw actuation is usually performed by an assistant, and then the ophthalmologist applies the injector in the preset mode by inserting the ejector nozzle into the eyeball at the anterior lens guide and then actuating the actuation element until the intraocular lens is driven into the posterior eye chamber.

SUMMARY OF THE INVENTION

The purpose of the invention is the further development of an injector for the implantation of an intraocular lens into a human eye, wherein the injector should exhibit the simplest possible switchability between the push actuation and the screw actuation of the actuation element for advancing the intraocular lens. In particular, it shall be possible to switch the operating mode between the push actuation and the screw actuation in such a way that the injector is otherwise to be used in the same way, but wherein the switchover between the push actuation and the screw actuation should be adjustable immediately before the injector is used.

This task is solved starting from an injector as disclosed herein in combination with the characteristic features. Advantageous embodiments of the invention are also disclosed herein.

The invention includes the technical teaching that a switch element is arranged to the base body, whereas the switch element is rotatable about the actuation axis or is displaceable in the actuation axis, whereas the switch element features at least one spring arm, having a thread engagement structure on an inner surface facing the external thread, whereas at the base body is formed an inner surface, which forms an operative contact with an outer surface of the spring arm, whereas the inner surface and/or the outer surface is formed inclined to the actuation axis at an angle, or the inner surface features an inner radius varying at least in sections in a circumferential direction about the actuation axis, so that upon rotation or upon displacement of the switch element an elastic deformation of the spring arm towards the actuation axis and away from the actuation axis can be generated, whereby the thread engagement structure can be selectively engaged or disengaged with the external thread.

The core idea of the invention is a switch element on the housing of the injector, which can be manually rotated or displaced between two actuation positions, and in a first actuation position of the switch element, the thread engagement structure on the spring arm engages with the external thread of the actuation element for screw actuation, and in a second actuation position of the switch element, the thread engagement structure on the spring arm is disengaged from the external thread of the actuation element, so that finally the push actuation of the injector is set.

Thus, if the switch element is rotated or shifted to the second actuation position, the spring arm or several spring arms, in particular two spring arms lying opposite to each other, can spring back outward elastically outwards in relation to the actuation axis, so that the thread engagement structure releases the external thread of the actuation element. According to the invention, the interaction between the inner surface on the base body and the spring arm is generated by an interaction contact, which is designed in such a way that, in the event of an axial or rotational displacement of the switch element on the base body, a movement of the spring arm on the switch element is generated, which occurs in a radial direction with respect to the actuation axis, namely that the spring arm can be moved towards the actuation axis and thus towards the external thread of the actuation element and away from it again.

The axial direction describes a direction extending along the actuation axis and a radial direction describes a direction perpendicular to the actuation axis. In this respect, the axial and radial directions are perpendicular to each other in the present sense.

In order to generate the movement in the spring arm by a movement of the switch element, in a first embodiment, at least one surface involved in the interaction contact, i.e. either the inner surface in or on the base body and/or the outer surface on the spring arm, features an inclination with an angle to the course of the actuation axis. The angle can be deduced between the actuation axis and a vector lying in the surface involved, i.e. the inner surface and/or the outer surface, wherein the vector runs through the contact point or the contact line between the inner surface and the outer surface and features an angular value greater than 0° and less than 90°. Of course, the inner surface and/or the outer surface of the switch element or the spring arm respectively may also be curved or otherwise deviate from a plane without deviating from the inventive idea of an interaction contact at an angle.

The inclination of the surface involved can be formed in the inner surface on the base body, while the outer surface of the spring arm is straight, i.e. extends approximately parallel to the actuation axis without any angular inclination. With the same effect, the outer surface of the spring arm can likewise feature an angle with the actuation axis, while the inner surface is straight and parallel to the actuation axis, in particular running cylindrically about the actuation axis; therein the inclined outer surface of the spring arm abuts for instance against an edge in inner surface and thereby likewise generates a radial elastic movement upon an axial displacement.

Of course, the inventive principle of interaction between the base body and the spring arm works particularly well if both the inner surface and the outer surface have an inclination or a curvature, which in particular each enclose the same angle to the actuation axis. In every embodiment of the inner surface and the outer surface, however, an interaction contact is formed, which is inclined at an angle relative to the actuation axis. The switch element does not have to be designed in one piece, but can also be multi-part, and the base body can likewise be designed in one or more parts. In this respect, the inner surface can also be formed within an annular body, for example, which is only arranged or fixed in an inner passage in the base body, wherein the annular body is nevertheless part of the base body in the sense of the present invention. Thus, an inner surface is also formed on the base body if the base body is designed in several parts and the inner surface is not formed directly on a main part of the base body, but on an additional element or the like.

In terms of the invention, the switch element also has a spring element if it is not designed in one piece and/or materially uniform with the body of the switch element, but is only arranged on the body of the switch element or is movable or interactively connected to the switch element, but is otherwise separable, for example.

For example, the switch element is designed as a pushing element and is arranged movably in or on the base body. Alternatively, the switch element is designed ring-shaped or hull-shaped and encloses the actuation element partially or completely and is displaceable or rotatable on the base body.

The inner surface is arranged on the base body in such a way that upon axial displacement of the switch element in the form of a pushing element, and thus also upon axial displacement of the at least one spring arm arranged on the switch element, relative to the base body, the displacement of the spring arm also occurs relative to the inner surface. Thus, the principle of the interaction contact at an angle to the actuation axis can be used in this respect also with a pushing element, which does not have to be rotated and can be displaced, for example, at only one circumferential position in or on the housing. In the preferred case, however, the switch element is ring-shaped or hull-shaped and the actuation element is partially or completely enclosed by the switch element.

With further advantage, at least the surfaces involved in the interaction contact can feature a coating, which allows the surfaces to slide off each other particularly well, i.e., that the inner and/or outer surfaces feature the coating.

Advantageously, the base body has a receiving section with a passage, through which the actuation element extends, and wherein the switch element is received at or on the receiving section so as to be axially movable along the actuation axis and/or rotatable about the actuation axis. The switch element can also be inserted into the receiving section on the inside, in particular if the receiving section is hull-shaped, wherein manual adjustability from the outside by the user must be ensured. With particular advantage, the switch element can feature a hull section, which is mounted on the outside of the receiving section in a rotatable or displaceable manner, and the spring arm or the several spring arms embrace the open end of the receiving section and project into it on the inside, in particular to such an extent that the end of the spring arm or the ends of the spring arms project into the annular gap between the actuation element and the inner surface of the base body.

It is advantageous that the inner surface is formed on the inside of the receiving section of the base body. This results in an advantageous geometry, because the spring arms do not have to be unnecessarily long. An arrangement of the inner surface for interaction with the spring arm(s) is, however, also possible within the scope of the invention on the inside in a cavity in the base body located further to the front of the injector.

The at least one spring arm is thus arranged on the switch element in such a way that the spring arm extends at least partly between the actuation element and the inner surface in the base body and/or extends into the receiving section.

According to a first embodiment, the inner surface forms at least partly an inner cone in the base body. The effect of the radial approach of the at least one spring arm and its elastic radially outwardly directed rebounding is thereby generated by an axial displacement of the switch element and thus of the at least one spring arm along the actuation axis, wherein the axial displacement of the switch element can be generated, for example, by means of a rotational movement of the switch element on the receiving section. In this respect, the spring arms in the inner cone rotate with a rotation of the switch element about the actuation axis, but this does not interfere with the function of the radial movement of the spring arms.

According to a second embodiment, the inner surface with the inner radius varying in a circumferential direction is formed on a circumferential segment about the actuation axis in the base body, wherein the circumferential segment extends on a circumference with a circumferential angle of 360° or with a circumferential angle of 180° or with a circumferential angle of 120° or with a circumferential angle of 90°. According to the number of circumferential segments, it is advantageous to assign a spring arm to each circumferential segment. In particular, it is provided that at least one spring arm, two spring arms facing each other, three, four or more spring arms are arranged on the actuator.

An inner surface with the circumferentially varying inner radius causes the at least one spring arm to be pressed radially inwards when the actuator is rotated into a first actuation position, if the inner radius is smaller at this point, so that the thread engagement structure engages with the external thread. For this purpose, the outer surface of the spring arm, in particular on the rear side of the internal thread engagement structure, is in contact with the inner surface of the base body, and the inner surface tightens around the spring arm for this purpose to some extent, since the spring arms rotate with a rotation of the switch element within the inner surface and come into contact with different circumferential positions of the inner surface and consequently with different inner radii. When rotating back in the opposite direction, the spring arms again come into contact with a larger inner radius of the inner surface, so that the spring arm(s) spring back outwards independently and elastically. The spring arms can be rotated along with the rotation of the switch element, so that they also rotate about the actuation axis in the area of the inner surface of the base body when the switch element is rotated. The spring arms can also be arranged only indirectly on the switch element.

In particular, the switch element is designed without thread. In this way, the injector can be switched between the operating modes of push actuation and screw actuation with a simple switch element in the form of a rotatable ring or a slewing ring without having to fold down an element on the outside of the injector and thus change the handling. The switch element can be labeled, for example "Push" and "Screw", and arrows can be applied to the switch element, so that the user can easily and immediately recognize in which direction the switch element must be rotated about the actuation axis in order to activate either the push or screw actuation. The contact between the spring arm and the housing in the area of the inner surface need not be a direct contact within the scope of the invention, and additional elements may be interposed, which also enable the force-transmitting contact in the sense of the invention.

At least one groove and one pin are formed advantageously between the receiving section and the switch element, wherein the pin is guided in the groove. Preferably, the at least one groove is provided approximately on the outer circumference of the receiving section, wherein the at least one pin is formed on the inside of the switch element and guided in the groove. In particular, the switch element can be arranged on the receiving section by means of a threaded connection, so that upon rotation of the switch element about the actuation axis, the switch element executes a movement along the actuation axis.

If the inner surface is designed with a circumferential segment according to the second embodiment with a varying inner radius, then preferably at least one groove is provided circumferentially about the actuation axis at an axial position only between the receiving section and the switch element, since in this variant the switch element and thus the at least one spring arm does not have to be displaced axially in the actuation axis but only rotated about it.

If the switch element is ring-shaped or hull-shaped, it is not necessarily but preferably arranged on the base body in such a way, that the axis of rotation of the ring-shaped or hull-shaped switch element coincides with the actuation axis.

The handling of the injector with a rotatable switch element is generally easier and more convenient than pushing a pushing element axially between two detent positions. However, it is also conceivable that a ring-shaped or hull-shaped switch element can likewise be moved in the actuation axis on the base body, i.e. it can be moved between two detent positions.

Finally, for the first embodiment, it is provided that the switch element features a push/rotate movability in arrangement on the base body, from which the most preferred variant is obtained, namely when the switch element can be axially displaced on the base body with a thread-like guide between the switch element and the base body upon a rotation. If the switch element is rotated manually and the switch element and the base body interact via a corresponding thread-like guide, the axial displacement of the switch element in the actuation axis can be achieved very comfortably in this way.

It is also conceivable that the switch element is arranged in a fixed axial position and can be rotated on the base body, and still the inner surface features the form of the inner cone. This design is possible if for the axial displacement of the spring arm(s) an arrangement of the at least one spring arm is decoupled at the switch element in such a way, that these are also moved axially by the switch element, for example via a separate crank mechanism or the like, when the switch element is rotated, similar to a ballpoint pen, which can retract or extend a refill when a front or rear part is rotated. Such an interaction is also encompassed by an arrangement of the at least one spring arm on the switch element.

Moreover, the base body may feature a wing handle, wherein the receiving section adjoins the rear side of the wing handle as an extension. The receiving section, the wing handle and the further, remaining base body preferably but not restrictively can be designed in one piece and of the same material and can be manufactured especially by injection moulding.

Furthermore, it is advantageous if the injector features a receiving means for a lens cartridge, wherein an intraocular lens is inserted into the lens cartridge, and wherein the lens cartridge with the intraocular lens can be inserted into the receiving means. Such injectors can, in particular, be reusable, provided they can be re-sterilized. However, an injector that can be loaded with a cartridge can also be designed as a disposable article.

The injector can also be designed as a so-called pre-load system, according to which the injector features a receiving chamber, which is formed in the base body and/or in a lens guide arranged at the front end of the base body, and in which an intraocular lens is inserted, so that the injector forms an individually manageable and tradable unit with the inserted intraocular lens. In this respect, the injector according to the invention can function as a pre-load system or as a cartridge system.

Finally, a piston is received in the base body and can be displaced axially by the actuation element via a rotary joint. Especially when the screw actuation of the injector is switched on, the actuation element has to perform the rotational movement, while the piston only performs a linear movement in the actuation axis without rotating about the actuation axis.

The base body is advantageously formed in one piece with the receiving section and with the wing handle from a plastic body, wherein the lens guide with a tip-side ejection nozzle for ejecting the intraocular lens is arranged, in particular detachable, at the front end of the base body.

BRIEF DESCRIPTION OF THE DRAWINGS

Further measures to improve the invention are described in more detail below, together with a description of preferred implementation examples of the invention using the figures. It shows:

FIG. 5 a cross-sectional view of the injector in the area of the inner surface, which, according to a second embodiment, features an inner radius varying circumferentially about the actuation axis, and wherein the spring arms shown do not engage with the external thread of the actuation element; and FIG. 6 the cross-sectional view of the injector in the area of the inner surface as shown in FIG. 5, with the spring arms shown engaging with the external thread of the actuator.

DETAILED DESCRIPTION OF THE INVENTION

Figure 1:
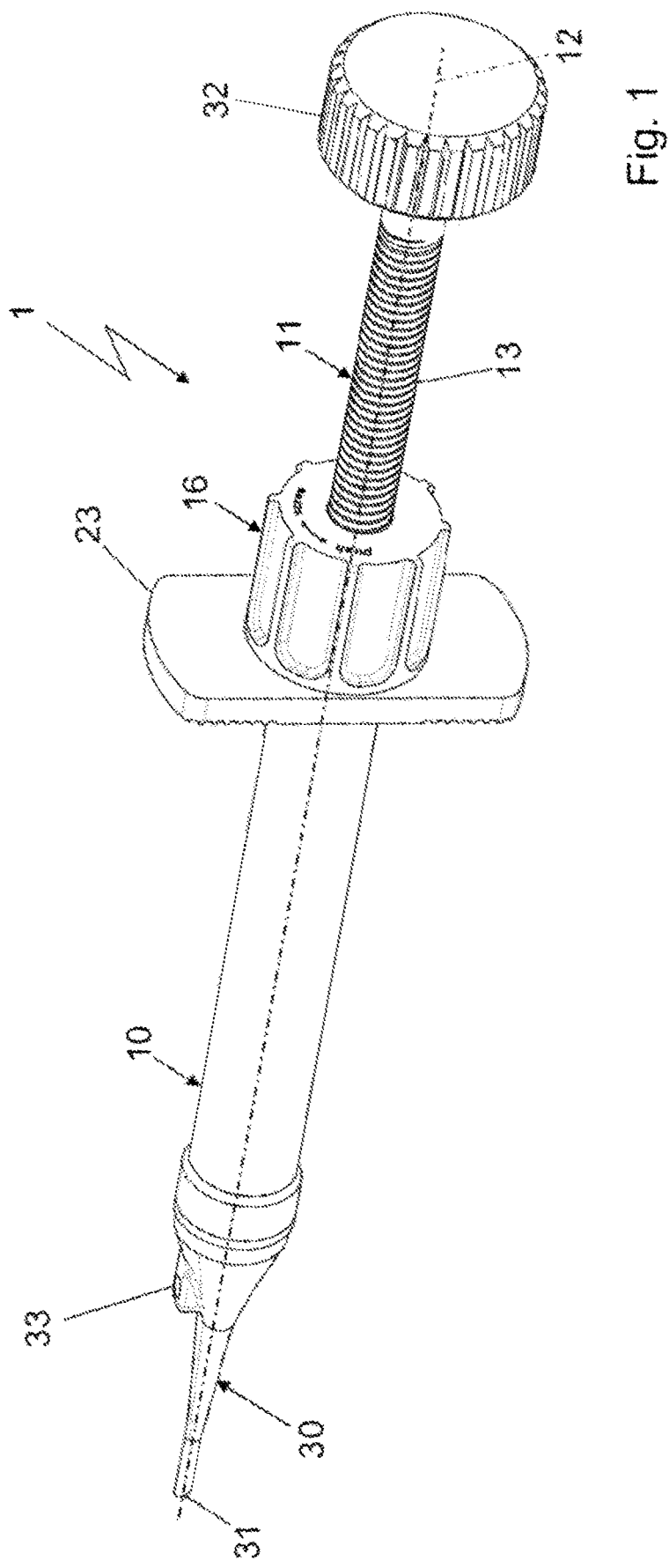
FIG. 1 a perspective view of the injector for implantation of an intraocular lens into a human or animal eye.

FIG. 1 shows a perspective view of the injector 1, which is used to implant an intraocular lens into a human or animal eye. The injector 1 has a base body 10 as its main structural component, and an elongated actuation element 11 with a handle 32 at the rear end is partially inserted into the base body 10. The actuation element 11 has a section with an external thread 13 over its essential length, and the actuation element 11 is inserted in sections from the rear into the base body 10 in such a way that the handle 32 is formed at a free end of the actuation element 11.

At the front side of the base body 10, a lens guide 30 is arranged in which the intraocular lens is inserted in a manner not shown closer. The main component of the base body 10 is approximately cylindrical or ergonomically designed for handling by a human hand and has an elongated extension, and the injector 1 with the base body 10, with the lens guide 30 at the front and with the actuation element 11 inserted at the rear extends longitudinally in an actuation axis 12. The actuation axis 12 simultaneously forms the displacement axis and the rotation axis for the optionally displaceable or rotatable actuation element 11.

For improved handling there is a wing handle 23 on the rear part of the base body 10, so that the injector 1 can be grabbed between the index finger and the middle finger with the wing handle 23, while the user can push the handle 32 on the rear side with the thumb when the push actuation is set.

At the back of the wing handle 23 follows a switch element 16, which is mounted on the base body 10 so that it can rotate about the actuation axis 12, and the switch element 16 has a passage through which the actuation element 11 extends. The switch element 16 is set up on the base body 10 in such a way that it does not interact with the actuation element 11 via a threaded connection.

On the lens guide 30, a load opening 33 is shown through which a viscoelastic can be inserted before the injector is operated. The viscoelastic then wets the inserted intraocular lens and the inner lumen, especially in the lens guide 30, in order to promote the process of expelling the intraocular lens or to enable the intraocular lens to be expelled without damage.

The switch element 16 of the injector 1 forms a means to switch the operating mode of the injector 1 between a push actuation and a screw actuation. In the embodiment shown in FIG. 1, the switch element 16 is designed to rotate about the actuation axis 12 on the base body 10 for switching between the push actuation and the screw actuation. The interaction of the switch element 16 with the actuation element 11 is shown in more detail in the following Figures. According to the following embodiment, the switch element 16 can also be moved axially along the actuation axis 12 without being rotated in order to achieve the same effect of switching between screw and push actuation.

Figure 2:
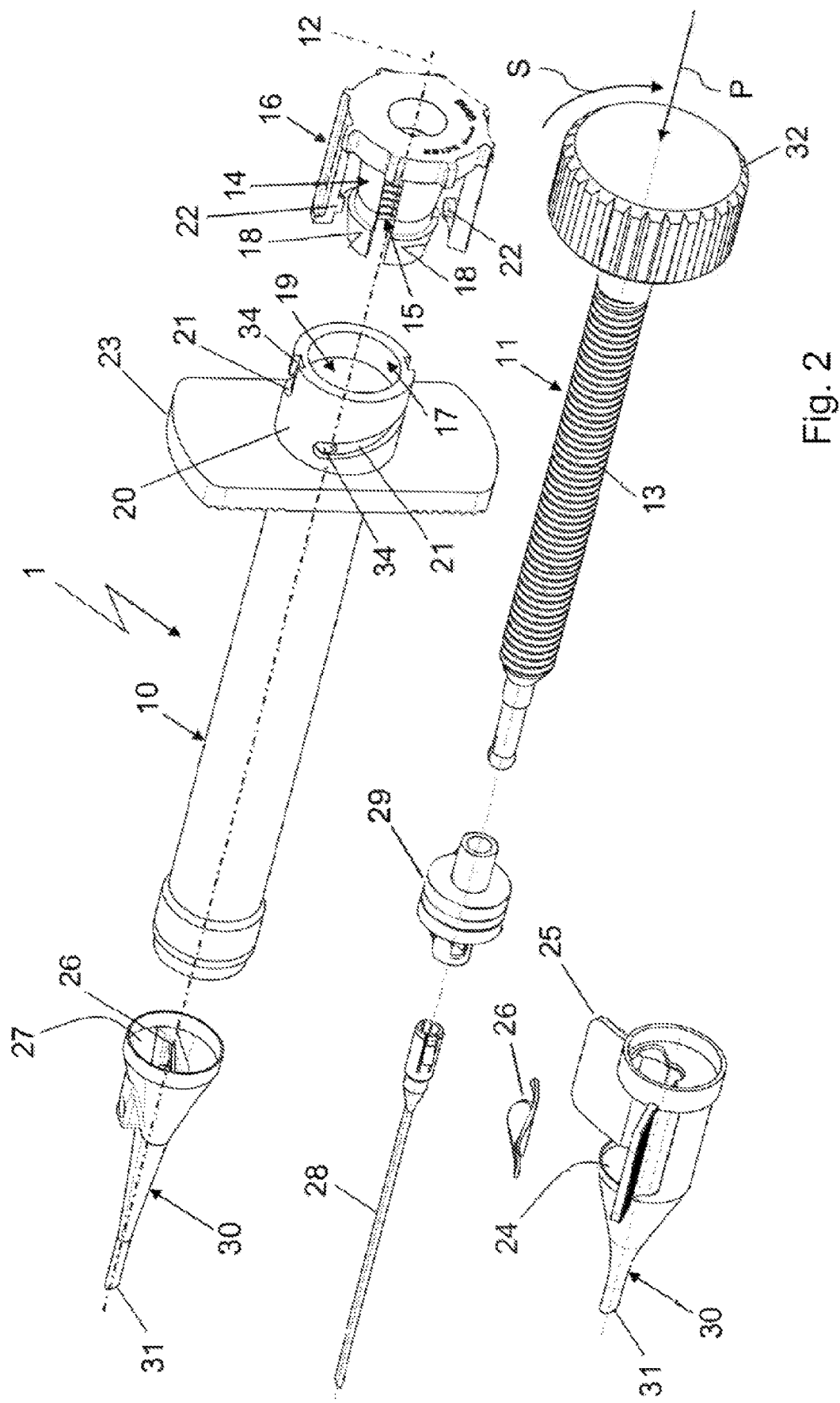
FIG. 2 an exploded view of the main components of the injector as shown in FIG. 1.

FIG. 2 shows a non-exclusive, but preferred embodiment of the injector 1 in an exploded view, in which the essential components of the injector 1 are exemplarily shown, wherein further components of the injector 1 are present, which are not shown, since they are not necessary for the presentation of the present invention, but which are also components of the injector 1 according to the invention, so that the illustration is not to be understood conclusively, wherein in particular means for acting on the intraocular lens are to be understood.

The illustration shows the base body 10 in isolation, and a first lens guide 30, shown in alignment with the actuation axis 12, is designed with a receiving chamber 27, in which an intraocular lens 26 is inserted (visible by one of the haptics), and a second lens guide 30, shown alternatively at the bottom, represents an alternative design to the first lens guide 30 and features a receiving means 24 for receiving a lens cartridge 25, in which the individually shown intraocular lens 26 is inserted. If the intraocular lens 26 is inserted into the lens cartridge 25 and the lens cartridge 25 is then inserted into the receiving means 24, the intraocular lens 26 can be expelled out of the tip of the expulsion nozzle 31 into the posterior chamber of the human or animal eye by means of a piston 28. If the injector 1 is designed as a pre-load system, the lens guide 30 shown above can be used, which has the receiving chamber 27, in which the intraocular lens 26 can already be inserted by the manufacturer in order to make the pre-load system commercially available as a ready-to-use unit already containing the intraocular lens.

To expel the intraocular lens 26, the piston 28 performs a linear movement in the actuation axis 12, and if the actuation element 11 is screwed into the base body 10 in the operating mode of screw actuation S, a rotary joint 29 is used to ensure that the rotational movement of the actuation element 11 is not transmitted to the piston 28.

If the lens guide 30 is not used with the intraocular lens 26 directly contained in the receiving chamber 27, the lens guide 30 featuring the receiving means 24, into which the lens cartridge 25 with an intraocular lens 26 can be inserted, can be used alternatively. In this case, the lens guide 30 with the receiving chamber 27 forms the pre-load system, according to which the injector 1 is sold with the intraocular lens 26 already inserted at the factory. Alternatively, the injector 1 can also be offered without the pre-loaded intraocular lens 26, for which the lens guide 30 has the receiving means 24, into which the lens cartridge 25 with the intraocular lens 26 can only be inserted immediately before the injector 1 is used, which is called a cartridge system. The receiving means 24 for receiving a lens cartridge 25 and/or the receiving chamber 27 for directly receiving an intraocular lens 26 can alternatively be arranged in the base body 10 instead of in the lens guide 30, or the receiving means 24 or the receiving chamber 27 are formed in a spatial area between the lens guide 30 and the base body 10 if the lens guide 30 is arranged on the base body 10.

Behind the wing handle 23, the base body 10 features an integrated receiving section 20, to which the switch element 16 is attached rotatably about the actuation axis 12 and/or axially displaceable. The outer surface of the receiving section 20 features a groove 21, which is spirally inserted into the receiving section 20, so that when the switch element 16 is rotated about the actuation axis 12, the switch element 16 simultaneously executes a movement in the actuation axis 12. At the end sections of the groove 21, snapping means 34 can be present, and if the switch element 16 is rotated into the respective end position, the user receives a haptic feedback and the switch element 16 automatically remains in the end position, which is important, since an axial force must be applied to the switch element 16 via the spring arms 14 during screw actuation. There are pins on the inside of the switch element 16, which are engaged in the groove 21 for an interaction, which are only not illustrated in the Figure shown.

The pick-up section 20 is hull-shaped and in particular connected in one piece with the base body 10 at the back of the wing handle 23 and the pick-up section 20 forms a part of the base body 10.

Within the pick-up section 20, an inner surface 17 is formed about the actuation axis 12. According to the embodiment shown, this inner surface 17 forms an inner cone 19 which has a diameter widening towards the open side of the receiving section 20. The inner surface 17 is shown as a surface on the inside of the base body 10. However, since the base body 10 can also be designed in several parts, the inner surface 17 can also be designed on a single part, for example in the form of an insertable ring, which nevertheless belongs to the base body 10 in the sense of the invention and forms a component part of it.

Several spring arms 14 are arranged at the switch element 16, which can be moved inwards by an elastic deformation inwards in the direction towards the actuation axis 12 or automatically spring back outwards away from the actuation axis 12. In an unloaded arrangement of the spring arms 14, they have a distance to each other or to the actuation axis 12, according to which the external thread 13 on the actuation element 11 can be moved axially freely between the spring arms 14. The delivery condition of the injector 1 should therefore be set up with the switch element 16 in a position, in which it is in the actuation position for push actuation P, so that the spring arms 14 are not permanently loaded with force and retain their spring-back effect over a longer storage period.

An axial displacement of the switch element 16 in the actuation axis 12 generates an elastic spring movement of the spring arms 14 in the direction towards the central actuation axis 12. In particular, if the switch element 16 is displaced towards the wing handle 23, preferably by a rotation, the displacement of the switch element 16 in the actuation axis 12 towards the wing handle 23 is caused by the guidance of the groove 21. Through the contact of the outer surfaces 18 of the spring arms 14 with the conical inner surface 17 in the base body 10, the spring arms 14 elastically spring inwards towards the actuation axis 12 when the switch element 16 is displaced in the direction of the wing handle 23, so that a thread engagement structure 15 on the inside of the spring arms 14, shown here only indirectly as a dotted line, can engage with the external thread 13 of the actuation element 11 in order to then set the injector 1 for screw actuation S.

If the spring arms 14 spring back radially outwards during an axial displacement of the switch element 16 away from the wing handle 23, in particular by a backward rotation, by bringing the outer surfaces 18 of the spring arms 14 into contact with the inner surface 17 in its area of larger diameter, the push actuation P of the injector 1 can be set, since the spring arms 14 are no longer in engagement with the outer thread 13 of the actuation element 11.

Figure 3:
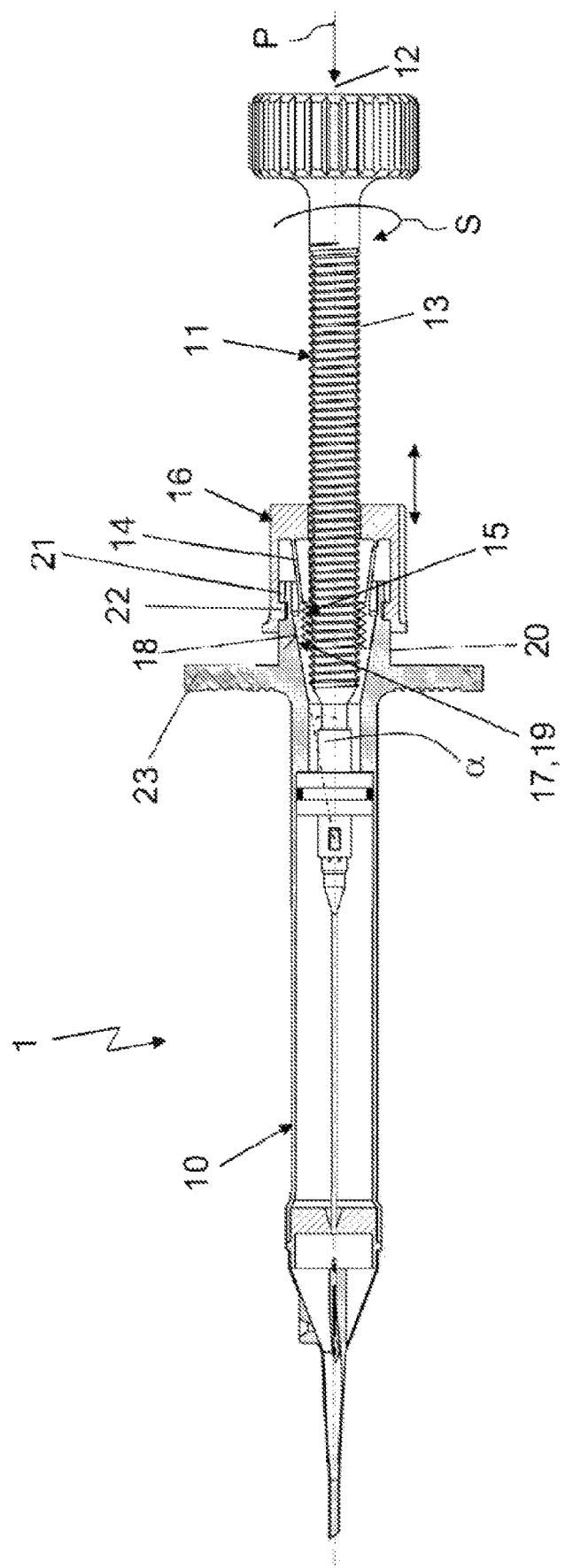
FIG. 3 a cross sectional view of the injector according to a first embodiment with an inner surface in its base body forming an inner cone.

FIG. 3 shows a first embodiment of injector 1 in a cross-sectional view. The illustration shows the base body 10 with the wing handle 23, and on the rear side of the wing handle 23 there is a receiving section 20, which is designed in one piece with the base body 10 and extends together with the base body 10 along the actuation axis 12. The switch element 16 is mounted on the receiving section 20 and the actuation element 11 with the external thread 13 is inserted into the base body 10 at the rear.

A groove 21 is provided in the outer surface of the receiving section 20 and a pin 22 is located on the inside of the switch element 16, which projects into the groove 21 and is guided in it. If the switch element 16 is rotated according to the arrow shown, it can be displaced axially along the actuation axis 12 as indicated by a double arrow. Thus, if the switch element 16 is rotated in a first direction of rotation about the actuation axis 12, the switch element 16 approaches the wing handle 23, for example, by displacing it to the left along the actuation axis 12. If the switch element 16 is rotated in an opposite direction, the distance to the wing handle 23 increases again and the switch element 16 moves to the right along the actuation axis 12.

On the inside of the switch element 16, spring arms 14 are formed, which interact in a special way with the base body 10. Within the receiving section 20 an inner surface 17 is formed on the base body 10, which extends in particular rotationally symmetrically about the actuation axis 12. The inner surface 17 is designed so that an inner cone 19 is formed above the inner surface 17. The inner cone 19 is thus formed within the receiving section 20 in such a shape, that the cone expands in the direction of the free opening of the receiving section 20. The example shows the inner surface 17 in the area of the receiving section 20, but it can also be positioned further inside the base body 10, for example in or at the position of the wing handle 23.

The switch element 16 encompasses the receiving section 20, and the spring arms 14 have outer surfaces 18, which are in interaction contact with the inner surface 17. The inclination of the inner surface 17 formed at the angle α results in a radial deflection of the spring arms 14 towards the actuation axis 12 when the switch element 16 is displaced in the direction of the wing handle 23. If the switch element 16 is moved back in such a way that the distance to the wing handle 23 increases, the spring arms 14 spring back and the distance to the actuation axis 12 increases again.

The spring arms 14 each have a thread engagement structure 15 on the inside, which engages with the external thread 13 of the actuation element 11 when the switch element 16 is displaced in the direction of the wing handle 23 by a rotation. During this process, the outer surfaces 18 move along the inner surface 17 and the spring arms 14 are pressed radially inwards due to the shape of the inner cone 19. If the spring arms 14 are in engagement with the external thread 13 due to the inward deflection of the spring arms 14, the injector 1 can be operated with the screw actuation S. In this case, the thread engagement structures 15 on the inside of the spring arms 14 form a kind of internal thread or thread passage for the external thread 13 of the actuation element 11, so that the actuation element 11 can be screwed into the base body 10 in a very normal way. One or two thread segments are sufficient as thread engagement structure 15 and consequently one or two spring arms 14 are sufficient.

If the switch element 16 is shifted back to the right by back rotation so that the distance to the wing handle 23 increases, the spring arms 14 can spring back elastically by moving the outer surfaces 18 to a larger diameter of the inner surface 17 in the shape of the inner cone 19 while maintaining the interaction contact. As a result, the thread engagement structures 15 on the inside of the spring arms 14 are disengaged from the external thread 13 of the actuation element 11, and the actuation element 11 can be displaced axially along the actuation axis 12 without the need to introduce a screw movement into the actuation element 11. This allows the injector 1 to be operated by the push actuation P.

To ensure that the axial displacement of the switch element 16 along the actuation axis 12 is generated, the groove 21 can be formed helically or spirally on the outer circumferential surface of the receiving section 20. For this purpose, one groove 21 is sufficient. For better guidance and stabilization of the switch element 16, two or more grooves 21 may also be provided on the receiving section 20, each of which may have an identical, approximately spiral or S-shaped course about the actuation axis 12 with a gradient to produce the axial movement in the switch element 16.

Figure 4:
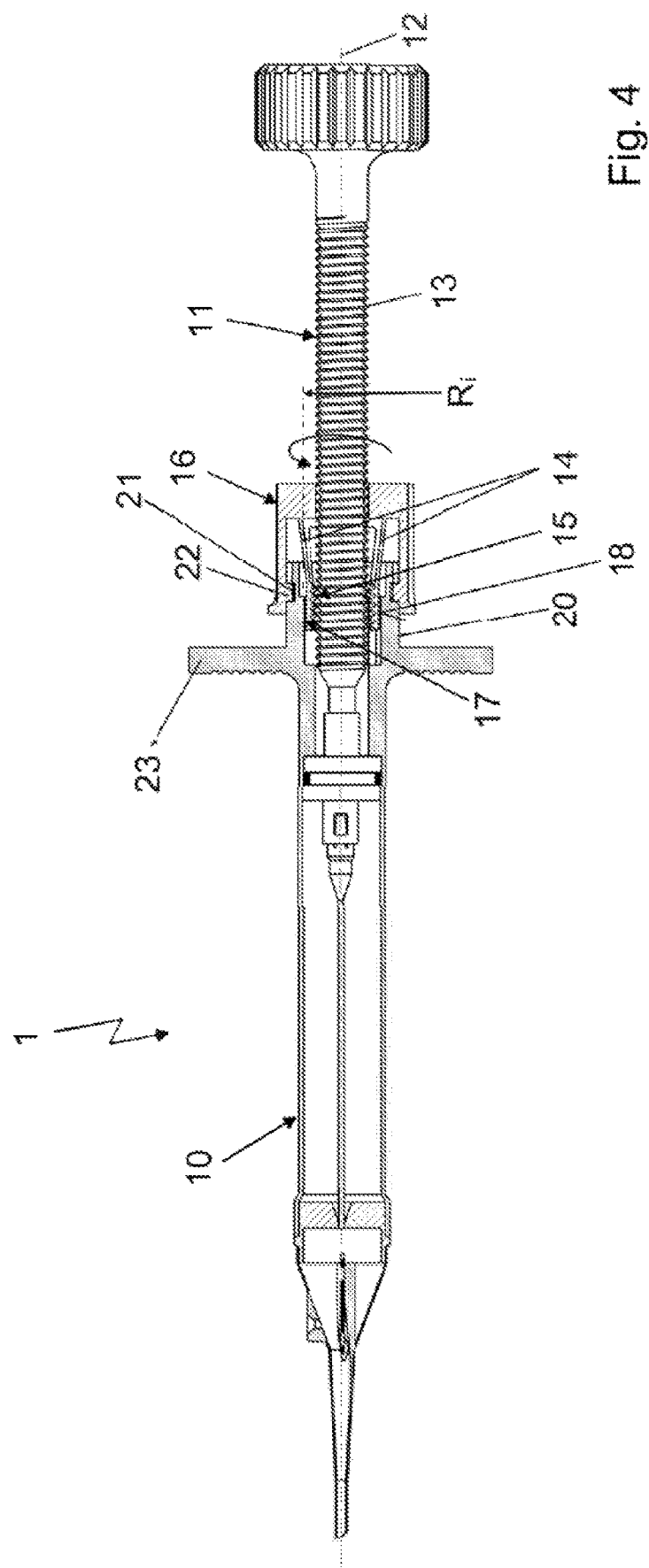
FIG. 4 a cross sectional view of the injector according to a second embodiment with an inner surface in its base body featuring a circumferentially varying inner radius about the actuation axis.

FIG. 4 shows a second embodiment of the injector 1 in a cross-sectional view with a modified inner surface 17, which has a varying inner radius Ri over the circumference. Due to the varying inner radius Ri, a rotation of the switch element 16 can also cause an elastic deformation of the spring arms 14 towards and away from the actuation axis 12 by simply rotating the switch element 16 without axial displacement on the receiving section 20. For this purpose, the groove 21 can run in circumferential direction without a pitch, so that when the switch element 16 is rotated, it maintains a constant distance to the wing handle 23. At least one pin 22 on the inside of the switch element 16 is used to guide the switch element 16, which runs in the groove 21. In the end positions of the rotary adjustment of the switch element 16, detent steps can be inserted in the groove 21 in order to provide the user with a pleasant haptic feedback that the respective end position representing the push or screw actuation has been reached.

If the switch element 16 is in a rotational position, in which the spring arms 14 deflect radially inwards, the thread engagement structures 15 on the inside of the spring arms 14 also engage with the external thread 13 of the actuation element 11. When the switch element 16 is rotated back about the actuation axis 12, the spring arms 14 spring back elastically, so that the thread engagement structures 15 are again disengaged from the external thread 13 of the actuation element 11.

The inner surface 17 with the inner radius Ri, which varies over the circumference or in the circumferential direction, is only shown as an example on the inside in the receiving section 20, and the inner surface 17 can also be located within the wing handle 23 or further forward in the passage of the base body 10. The inner surface 17 can also be located at an individual part of the base body 10, for example at a corresponding ring element, which is also part of the base body 10 in the sense of the invention.

FIGS. 5 and 6 show a cross-sectional view through the base body 10, represented by the wing handle 23. The actuation element 11 extends into the inner passage in the base body 10, which is shown cut so that the actuation axis 12 is perpendicular to the plane of the Figures. Through the cross-section, the spring arms 14 can be seen at least partially, which are located between the inner surface 17 in the base body 10 and the actuation element 11. In FIG. 5 the spring arms 14 are radially spaced apart from the actuation element 11 and in FIG. 6 the spring arms 14 engage with the external thread 13 of the actuation element 11.

The shown inner surface 17 with a circumferentially varying inner radius Ri illustrates a possible variant to generate a radial adjustment of the spring arms 14 by bringing the spring arms 14 into different circumferential positions with the inner surface 17.

FIG. 5 shows the position of the spring arms 14 enabling push actuation, and FIG. 6 shows a position of the spring arms 14 enabling screw actuation.

To adjust the push actuation, the spring arms 14 are in contact with the inner surface 17 via their outer surfaces 18 at a circumferential position where the inner radius Ri is particularly large. The elastic spring-back of the spring arms 14 causes the thread engagement structure 15 to disengage from the external thread 13 on the actuation element 11.

As shown in FIG. 6, the spring arms 14 can be rotated clockwise by rotating the switch element not shown to a position enabling screw actuation. In this position, the outer surface 18 of the spring arm 14 is in contact with the inner surface 17 at a circumferential position where the inner radius Ri is particularly small, and the thread engagement structure 15 inside the spring arms 14 is brought into engagement with the external thread 13 on the actuation element 11. In this position, the actuation element 11 can only be screwed into the base body 10 by a screwing movement.

The invention is not limited in its embodiment to the preferred embodiment given above. Rather, a number of variants are conceivable which make use of the solution presented even if the design is fundamentally different. All features and/or advantages arising from the claims, the description or the Figures, including constructional details or spatial arrangements, may be essential to the invention, both individually and in various combinations.

LIST OF REFERENCES 1 injector
10 base body
11 actuation element
12 actuation axis
13 external thread
14 spring arm
15 thread engagement structure
16 switch element
17 inner surface
18 outer surface
19 inner cone
20 receiving section
21 groove
22 pin
23 wing handle
24 receiving means
25 lens cartridge
26 intraocular lens
27 receiving chamber
28 piston
29 rotary joint
30 lens guide
31 ejection nozzle
32 handle
33 load opening
34 snapping means
P push actuation
S screw actuation
Ri inner radius
a angle

The invention claimed is:

1. An injector for implantation of an intraocular lens, comprising:
a base body; and
an elongated actuation element which projects at least partly into a rear section of the base body and which is movably guided along an actuation axis, and wherein a movement of the actuation element into the base body is generated selectively by a push actuation along the actuation axis or by a screw actuation about the actuation axis, and wherein the actuation element features an external thread at least on one section;
wherein:
a switch element is arranged to the base body, the switch element being rotatable about the actuation axis or displaceable along the actuation axis;
the switch element features at least one spring arm, having a thread engagement structure on an inner surface facing the external thread; and
the base body has an inner surface, which forms an operative contact with an outer surface of the at least one spring arm;
the inner surface and/or the outer surface being formed inclined to the actuation axis at an angle; or
the inner surface features an inner radius varying at least in sections in a circumferential direction about the actuation axis, so that upon rotation or upon displacement of the switch element an elastic deformation of the spring arm towards the actuation axis and away from the actuation axis is generated, whereby the thread engagement structure can be selectively engaged or disengaged with the external thread.

2. The injector according to claim 1, wherein:
the switch element is a pushing element and is arranged movably in or on the base body; and/or
the switch element is ring-shaped or hull-shaped and encloses the actuation element partially or completely and is displaceable or rotatable on the base body.

3. The injector according to claim 1, wherein:
the base body has a receiving section with a passage, through which the actuation element extends; and
the switch element is received at or on the receiving section so as to be axially movable along the actuation axis and/or rotatable about the actuation axis.

4. The injector according to claim 3, wherein:
the inner surface is formed on an inside of the receiving section of the base body.

5. The injector according to claim 1, wherein:
the at least one spring arm is arranged on the switch element in such a way that the spring arm extends at least partly between the actuation element and the inner surface in the base body and/or extends into the receiving section.

6. The injector according to claim 1, wherein:
the inner surface forms at least partly an inner cone in the base body.

7. The injector according to claim 1, wherein:
the inner surface with the inner radius varying in a circumferential direction is formed on a circumferential segment about the actuation axis in the base body (10), the circumferential segment extending on a circumference with a circumferential angle of 360° or with a circumferential angle of 180° or with a circumferential angle of 120° or with a circumferential angle of 90°.

8. The injector according to claim 1, wherein:
the at least one spring arm comprises at least one spring arm, two spring arms (14) facing each other, or three, four or more spring arms are arranged on the switch element.

9. The injector according to claim 1, further comprising:
at least one groove and one pin formed between the receiving section and the switch element, the pin being guided in the groove.

10. The injector according to claim 1, wherein:
the switch element is arranged on the receiving section by a threaded connection, so that upon rotation of the switch element about the actuation axis, the switch element executes a movement along the actuation axis.

11. The injector according to claim 1, wherein:
the base body has a wing handle, the receiving section adjoining the rear side of the wing handle as an extension.

12. The injector according to claim 1, wherein:
the injector has a receiving means for a lens cartridge, an intraocular lens being inserted into the lens cartridge, and the lens cartridge with the intraocular lens is insertable into the receiving means.

13. The injector according to claim 1, wherein:
the injector has a receiving chamber, which is formed in the base body and/or in a lens guide arranged at a front end of the base body, and in which an intraocular lens (26) is inserted, so that the injector forms an individually manageable and tradable unit with the inserted intraocular lens.

14. The injector according to claim 1, further comprising:
a piston received in the base body and axially displaceable by the actuation element via a rotary joint.

\* \* \* \* \*